(12) United States Patent
Mukai (10) Patent No.: US 6,585,725 B1
(45) Date of Patent: Jul. 1, 2003

(54) LASER IRRADIATION METHOD FOR LASER TREATMENT AND LASER TREATMENT APPARATUS

(75) Inventor: Hideo Mukai, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/692,319

(22) Filed: Oct. 20, 2000

Related U.S. Application Data (63) Continuation-in-part of application No. 09/552,518, filed on Apr. 19, 2000, now abandoned.

(30) Foreign Application Priority Data

Apr. 20, 1999 (JP) .......................................... 11-112883
Oct. 22, 1999 (JP) .......................................... 11-300293

(51) Int. Cl.$^7$ ................................................ A61F 9/007
(52) U.S. Cl. ................................ 606/10; 606/5; 606/13; 606/17
(58) Field of Search ................................ 606/2, 3, 9–17

(56) References Cited

U.S. PATENT DOCUMENTS 4,653,495 A * 3/1987 Nanaumi ..................... 606/17
5,336,217 A * 8/1994 Buys et al. ................... 606/9
5,599,340 A    2/1997 Simon et al.
5,743,902 A    4/1998 Trost
5,971,978 A   10/1999 Mukai

* cited by examiner

*Primary Examiner*—David M. Shay
(74) *Attorney, Agent, or Firm*—Finnegan, Henderson, Farabow, Garrett & Dunner, L.L.P.

(57) ABSTRACT

Disclosed are a laser irradiation method for laser treatment performed by irradiating a treatment part of a patient with a treatment laser beam and a laser treatment apparatus for practicing the method. The method includes the steps of: setting a shape and size of an irradiation area to be irradiated with the laser beam; determining a scanning sequence of beam spots based on the shape and size of the irradiation area set in the setting step, a spot diameter of the laser beam, and a predetermined rule; and performing laser irradiation to the beam spots within the irradiation area in accordance with the scanning sequence determined in the determining step, wherein the predetermined rule is a rule that the beam spots continuously irradiated with the laser beam become nonadjacent and scanning lines continuously irradiated become nonadjacent.

3 Claims, 11 Drawing Sheets

LASER IRRADIATION METHOD FOR LASER TREATMENT AND LASER TREATMENT APPARATUS

This is a continuation-in-part application of U.S. patent application Ser. No. 09/552,518 filed Apr. 19, 2000 now abandoned. The entire disclosure of the prior application is hereby incorporated by reference herein in its entirely.

BACKGROUND OF THE INVENTION

1. Field of the Invention

The present invention relates to a laser irradiation method for laser treatment performed by irradiating a treatment part or site such as an affected part with a treatment laser beam and a laser treatment apparatus used for practicing the irradiation method.

2. Description of Related Art

Conventionally, there have been known laser treatment apparatus for performing depilation, wrinkle removal, and birthmark removal, etc. by irradiating a skin surrounding hair follicles or a skin having wrinkles or birthmarks with a treatment laser beam (simply referred to as a treatment beam hereinafter). For example, in laser depilation treatment, a treatment beam is irradiated to a skin surrounding hair follicles, and resultant heat is radiated to the hair roots and then cauterizes them, thus depilating the hairs. Known as an irradiation method of the treatment beam is the method of determining in advance an area (its shape, size, and others) to be irradiated in response to one irradiation command signal and then irradiating the treatment beam to the predetermined area while scanning so that beam spots (spot positions) of the treatment beam are arranged within the irradiation area.

Figure 5:
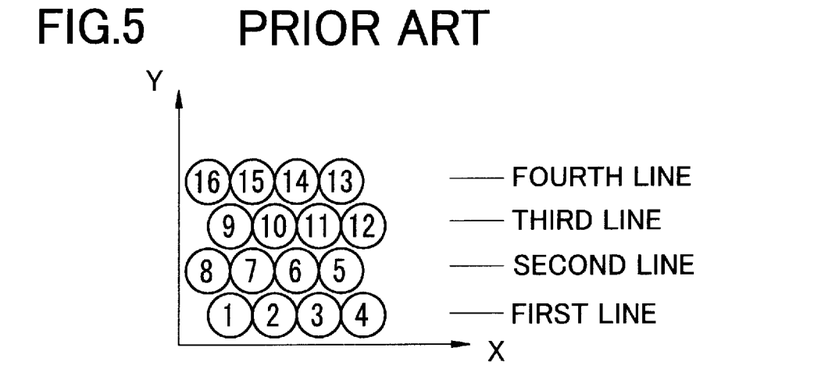
FIG. 5 is an explanatory view of a scanning pattern in a laser scanning method in the prior art.

However, it has been determined such that scanning the beam spots is made by causing the treatment beam to sequentially scan the irradiation area from an end spot in a first scanning line to a next, as shown in FIG. 5, and the scanning is repeated on a second scanning line immediately adjacent to the first scanning line, and then to a third scanning line. At this time, without considering the effects of a heat damping time in an immediately preceding irradiated spot, the treatment beam is irradiated to a next (immediately adjacent) spot, which is liable to cause the thermal damage to the skin.

It is to be noted that the heat damping time is defined as follows: when a treatment beam is irradiated to a target, the distribution of temperatures in a zone centered on the target is observed as a Gaussian distribution with the width which depends on the diameter of the zone; in relation to the Gaussian distribution, the heat damping time is interpreted as the time required until the center temperature of the Gaussian distribution decreases to 50% thereof.

Figure 11:
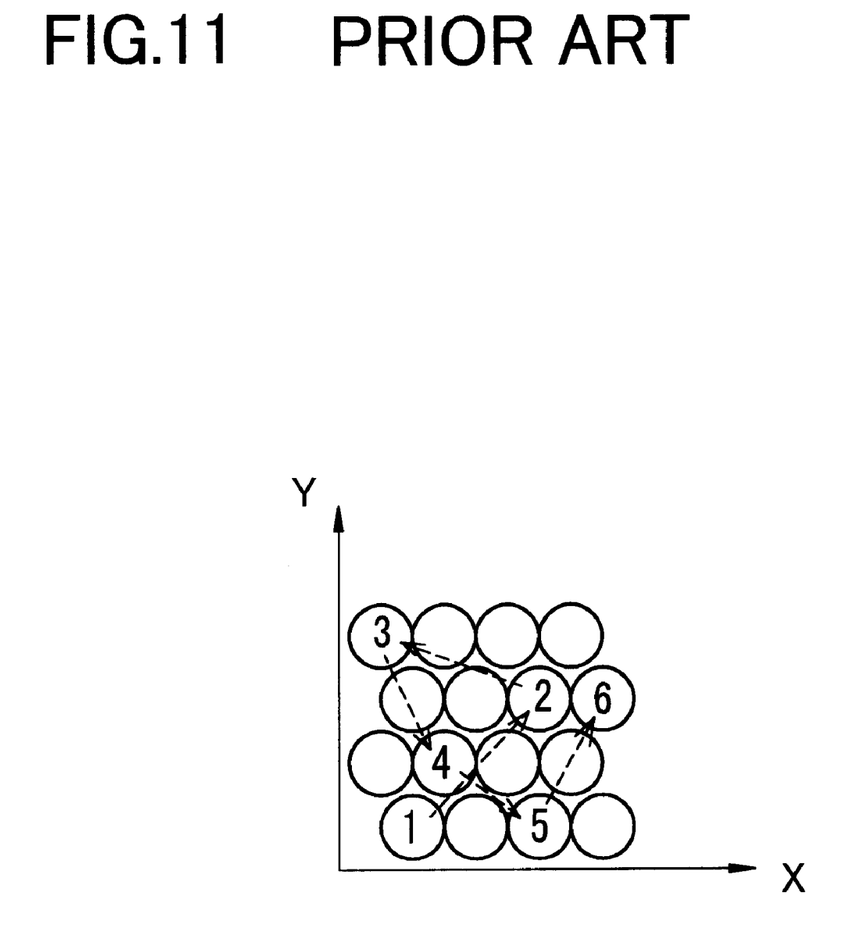
FIG. 11 is an explanatory view of a scanning pattern in another scanning method in the prior art.

For solving such the problem, there has been proposed a method of scanning the treatment beam over the irradiation area so that the beam spots of the treatment beam are arranged at random as shown in FIG. 11. However, there is no guarantee that the beam spots continuously irradiated will not be immediately adjacent to the immediately preceding irradiated spots. This method can predetermine a plurality of types of an irradiation area such as its shape, size and others, and memorize beforehand a scanning pattern (a scanning sequence) determined such that the beam spots irradiated continuously are arranged without becoming immediately adjacent to each other. It however needs complicated operations to beforehand determine scanning patterns for every irradiation area. When a new irradiation area is set, furthermore, determination of a scanning pattern corresponding to the area also requires complicated operations.

Furthermore, in the conventional method of scanning beam spots, the treatment beam is irradiated to the skin even while the treatment beam is shifting from a beam spot to another. This would apply undesired heat energy to an affected part of the skin and also cause wasted power consumption.

SUMMARY OF THE INVENTION

The present invention has been made in view of the above circumstances and has an object to overcome the above problems and to provide a laser irradiation method for laser treatment enabling suppression of the thermal damage to a skin irradiated with a treatment laser beam, and a laser treatment apparatus used for practicing the method.

Another object of the present invention is providing a laser irradiation method for laser treatment enabling easy determination of a scanning sequence of beam spots without requiring complicated operations, and a laser treatment apparatus used for practicing the method.

Furthermore, the present invention has another object of providing a laser irradiation method for laser treatment capable of performing laser irradiation in an appropriate, efficient manner, and a laser treatment apparatus used for carrying out the method.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser irradiation method for laser treatment performed by irradiating a treatment part of a patient with a treatment laser beam, the method including the steps of: a. setting a shape and size of an irradiation area to be irradiated with the laser beam; b. determining a scanning sequence of beam spots based on the shape and size of the irradiation area set in the setting step, a spot diameter of the laser beam, and a predetermined rule; and c. performing laser irradiation to the beam spots within the irradiation area in accordance with the scanning sequence determined in the determining step; wherein the predetermined rule is a rule that the beam spots continuously irradiated with the laser beam become nonadjacent and scanning lines continuously irradiated become nonadjacent.

According to another aspect of the present invention, there is provided a laser treatment apparatus for performing treatment for a treatment part of a patient by irradiating the part with a treatment laser beam, the apparatus including: a light delivery optical system provided with a laser source for emitting a treatment laser beam, for forming the laser beam emitted from the laser source into a spot beam and delivering the beam to the treatment part to be irradiated; scanning means disposed in the light delivery optical system, for scanning the laser beam onto beam spots within an irradiation area having a predetermined shape and size; determining means for determining a scanning sequence of the beam spots to be scanned by the scanning means based on a shape and size of an irradiation area, a spot diameter of the laser beam, and a predetermined rule; and scanning control means for controlling the scanning means to perform laser irradiation based on the determined scanning sequence; wherein the predetermined rule is a rule that beam spots continuously irradiated with the laser beam become nonadjacent and scanning lines continuously irradiated become nonadjacent.

Furthermore, according to another aspect of the present invention, there is provided a laser treatment apparatus for performing treatment for a treatment part of a patient by irradiating the part with a treatment laser beam, the apparatus including: a light delivery optical system provided with a laser source, for emitting a treatment laser beam, for forming the laser beam emitted from the laser source into a spot beam and delivering the beam to the treatment part to be irradiated; scanning means disposed in the light delivery optical system, for scanning the laser beam onto beam spots within an irradiation area having a predetermined shape and size; scanning control means for controlling the scanning means to perform laser irradiation based on a predetermined scanning sequence; and irradiation control means for controlling the laser irradiation in correspondence with shifting of the laser beam from a beam spot to a next by the scanning means.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
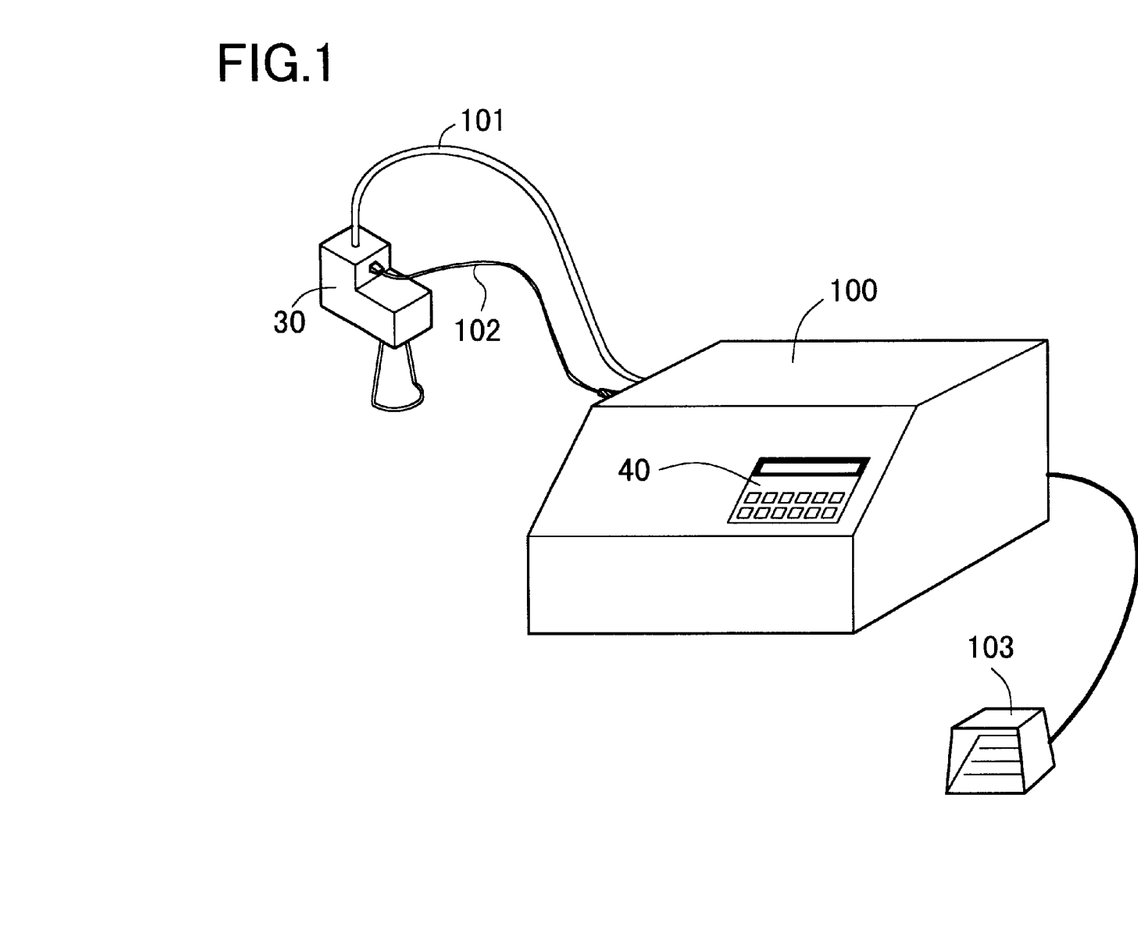
FIG. 1 is schematic perspective view of a laser treatment apparatus in an embodiment according to the present invention.
Figure 2:
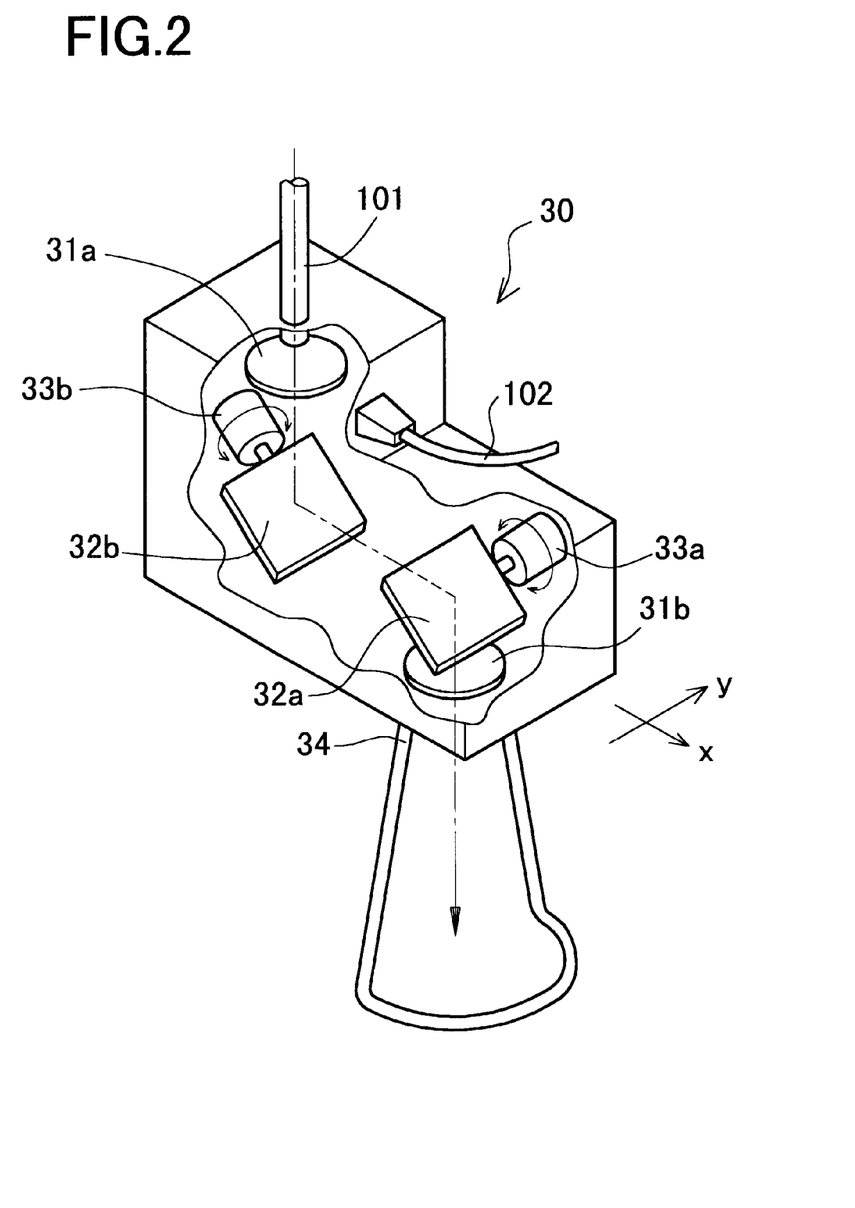
FIG. 2 is a schematic perspective view of a hand piece unit of the laser treatment apparatus, showing a part of an internal structure thereof.
Figure 4:
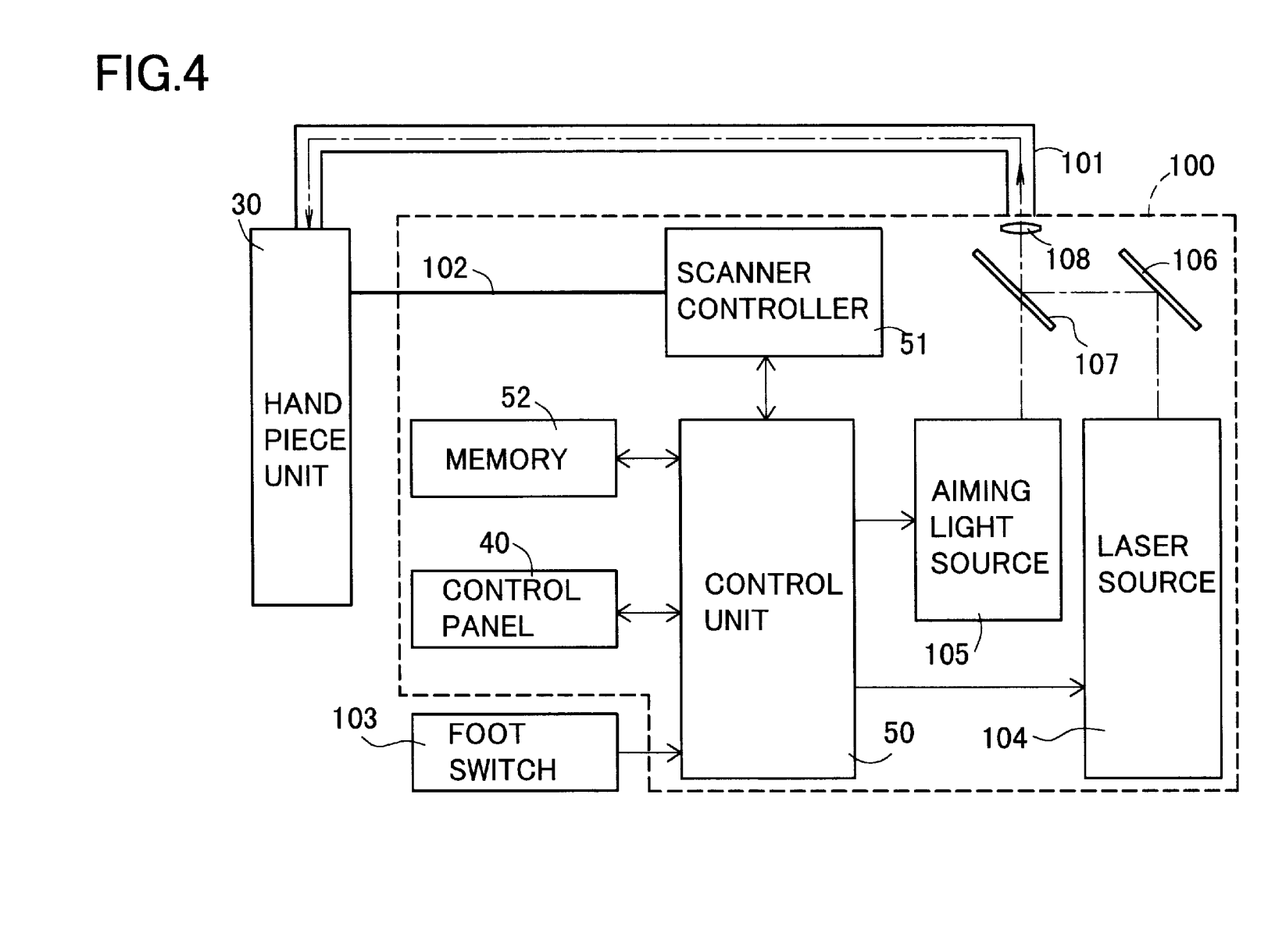
FIG. 4 is a block diagram of the principal elements of a control system and an optical system of the laser treatment apparatus in the embodiment.

A detailed description of preferred embodiments of a laser irradiation method for treatment and a laser treatment apparatus used for practicing the method embodying the present invention will now be given referring to the accompanying drawings. In the present embodiment, the laser irradiation method and the laser treatment apparatus therefor are applied to laser depilation. FIG. 1 is a schematic perspective view of the laser treatment apparatus for depilation. FIG. 2 is a schematic structural view of a hand piece unit 30 in the apparatus. FIG. 4 is a block diagram of the principal elements of a control system and an optical system (only a main unit 100 side is illustrated) of the apparatus.

Reference numeral 100 is a main unit of the apparatus, which contains a control unit 50, a laser source 104 for depilation, a laser source 105 for aiming light, and others. As the laser source 104 in the present embodiment is used a semiconductor laser source that emits laser light of a continuous wave (CW) with a wavelength of 835nm. As the laser source 105 is used a semiconductor laser source that emits laser light with a wavelength of 600 nm.

Reference numeral 40 is a control panel at which an operator inputs various settings of laser irradiation conditions such as shapes of irradiation area, sizes of irradiation area, and irradiation density, which will be mentioned later in detail. Reference numeral 101 is an optical fiber for delivering a treatment laser beam (which is referred below to as a treatment beam) coming therein from the main unit 100. Reference numeral 30 is a hand piece unit having a laser projecting port. Reference numeral 102 is a cable connecting the hand piece unit 30 to the main unit 100 (a scanner controller 51) for transmitting electrical signals for driving laser scanning mirrors 32a and 32b disposed in the hand piece unit 30. Reference numeral 103 is a foot switch for generating a trigger signal to start emission of the treatment beam.

The hand piece unit 30 is internally provided with lenses 31a and 31b for concentrating the treatment beam (and a laser beam for aiming, which is simply referred below to as an aiming beam) passed through the fiber 101 onto the skin of a patient to be treated, the driven mirrors 32a and 32b for scanning the treatment beam (and the aiming beam) onto the irradiation area in an X- and Y-axis directions, and drive motors 33a and 33b for driving the mirrors 32a and 32b respectively to independently swing. As the mirror 32a and the motor 33a in the present embodiment, a galvanomirror is used. The mirror 32b and the motor 33b have identical structures to the mirror 32a and the motor 33a. The treatment beam (and the aiming beam) is delivered from the main unit 100 to the hand piece unit 30 through the fiber 101. In the hand piece unit 30, the treatment beam (and the aiming beam) emerged from the fiber 101 is formed by the lenses 31a and 31b into a spot beam so that the beam is projected with a spot diameter of about 4 mm onto the irradiation area.

The motors 33a and 33b are controlled by a scanner controller 51 provided in the main unit 100. This scanner controller 51 transmits a control signal to the hand piece unit 30 through the cable 102, causing the motors 33a and 33b to rotate, thereby swinging the mirrors 32a and 32b. These swinging mirrors 32a and 32b scan the treatment beam (and the aiming beam) in a predetermined pattern (which will be mentioned later in detail) to beam spots within the irradiation area. Reference numeral 34 is a guide which is made contact with a patient s skin to be treated in order to put the hand piece unit 30 stably on the skin and keep the concentration distance of the treatment beam constant.

Figure 3:
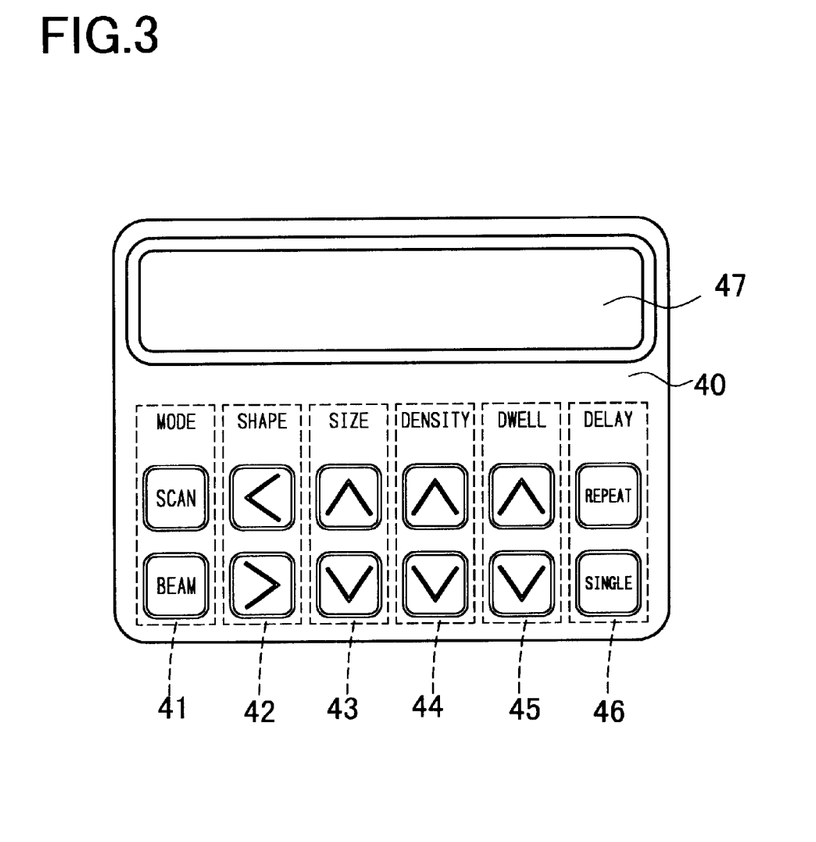
FIG. 3 is a plane view of a control panel of the laser treatment apparatus in the embodiment.

FIG. 3 is a plane view of the control panel 40 disposed on the main unit 100 and connected to the control unit 50. This control panel 40 is provided with various switches for setting or selecting irradiation conditions. Specifically, reference numeral 41 is a MODE selecting switch including a SCAN and BEAM buttons for selection between a SCAN mode of irradiating the treatment beam to the irradiation area while scanning the same and a BEAM mode of irradiating the treatment beam to one spot in the irradiation area without scanning. Reference numeral 42 is a SHAPE setting switch used for setting the shape of an irradiation area (a scanning area). In the present embodiment, using the switch 42, a desired shape can be selected from among four shapes; square, straight line, rectangle, and hexagon. Reference numeral 43 is a SIZE setting switch used for setting the size of the irradiation area having the shape determined with the switch 42. In the present embodiment, using the switch 43, a desired size can be selected from among several sizes prepared for each irradiation shape, which will be described later in detail.

Reference numeral 44 is a DENSITY setting switch used for setting the degree of overlap of beam spots (which is referred below to as "an irradiation density"). In the present embodiment, by using the switch 44, a desired irradiation density can be selected from among seven kinds; 0% (which is the irradiation density at which none of adjacent beam spots are overlapped each other), 5%, 10%, 15%, 20%, 25%, 30%.

Reference numeral 45 is a DWELL setting switch used for variably setting the duration of one irradiation in 5 msec. increments in the range of 10–100 msec. Reference numeral 46 is a DELAY setting switch including a REPEAT and SINGLE buttons to be used for determining whether irradiation is made OFF after completion of one scanning (SINGLE) or scanning is repeated (REPEAT). Reference numeral 47 is a monitor for displaying the irradiation conditions determined or selected using the above switches.

Figure 10:
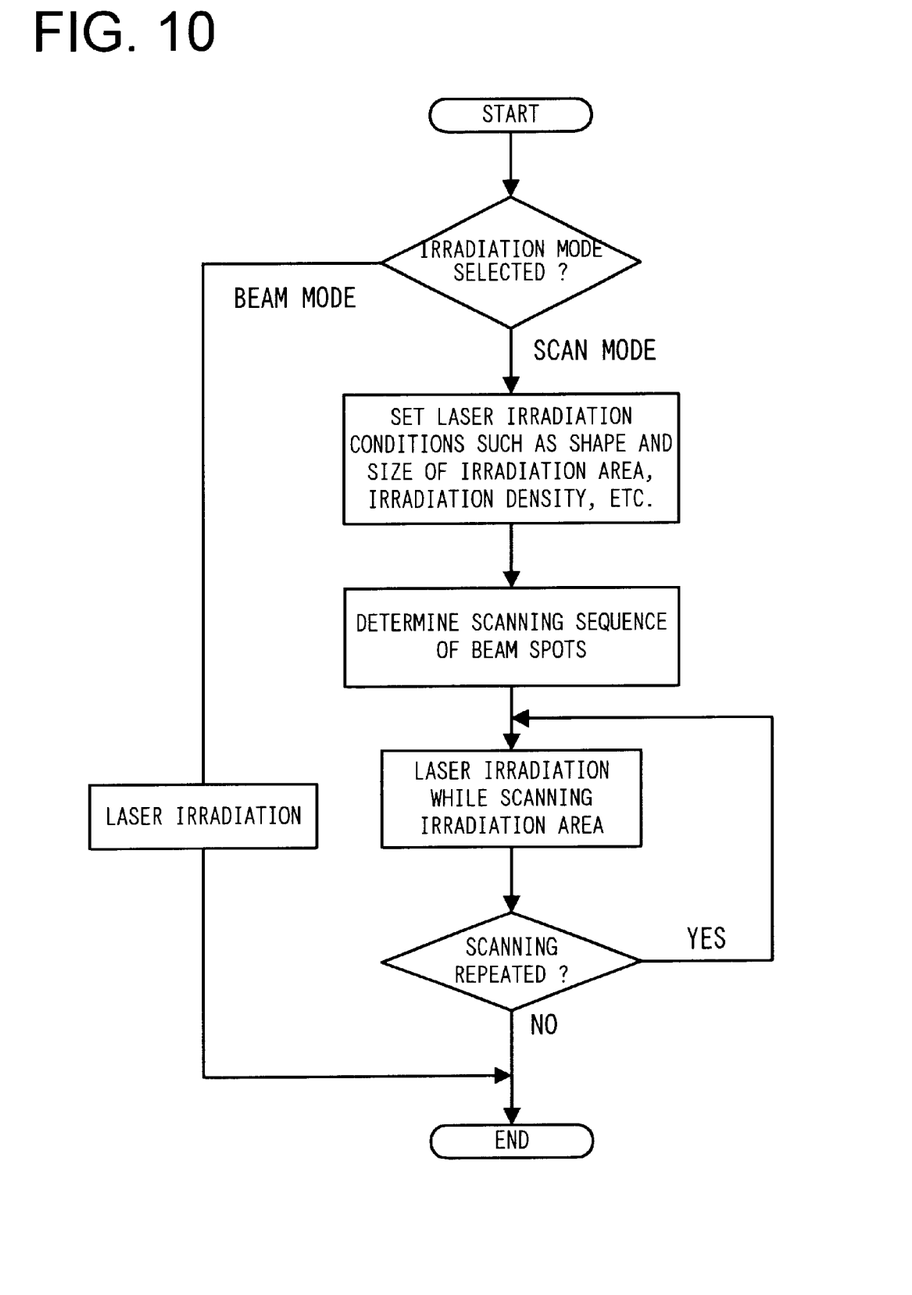
FIG. 10 is a flowchart of operating sequences of the laser irradiation apparatus in the embodiment.

Operation of the apparatus constructed as above will be next described with reference to FIGS. 4 and 10.

Upon application of electric power to the apparatus, the control unit 50 implements the diagnostic test for each section of the apparatus. When laser scanning is requested, the operator pushes the SCAN button of the MODE selecting switch 41 after completion of the diagnostic test to select the SCAN mode. Subsequently, the operator should put the hand piece unit 30 with the guide 34 made contact with the patient's skin in the vicinity of the treatment part or site so that the treatment beam projected from the hand piece unit 30 exactly may fall on the treatment part (depilation part) of the patient.

The hand piece unit 30 then projects the aiming beam delivered coaxially with the treatment beam to be emitted later. While visually confirming the irradiation spot (position) of the aiming beam on the treatment part, the operator can set the irradiation conditions by using the SHAPE switch 42, the SIZE switch 43, and the DENSITY switch 44.

Signals representative of the irradiation conditions set as above are transmitted to the scanner controller 51 via the control unit 50,. The scanner controller 51 then transmits a control signal tin accordance with the set irradiation conditions to the hand piece unit 30, thereby driving the motors 33a and 33b to swing the mirrors 32a and 32b, respectively. The aiming beam is thus irradiated to the patient's skin while scanning (or tracing) the contour of the irradiation area based on the shape and size determined as above, thereby allowing the operator to visually confirm the determined irradiation area.

Upon completion of setting of the irradiation conditions and identification of the irradiation area (i.e., confirmation of the shape land size of the irradiation area) through obser-vation of the aiming beam, the operator may depress the foot switch 103 to generate a trigger signal. When the trigger signal is entered, the control unit 50 causes the laser source 104 to emit the treatment beam. The treatment beam emitted from the laser source 104 is reflected by a mirror 106 and then a dichroic mirror 107 whereby the treatment beam is made coaxial with the aiming beam. Thereafter, the treatment beam (and the aiming beam) is condensed by a condenser lens 108 into the fiber 101. Through the fiber 101, the treatment beam (and the aiming beam) is delivered to the hand piece unit 30.

The trigger signal from the foot switch 103 is also transmitted to the scanner controller 51 via the control unit 50. The scanner controller 51 then transmits the control signal in accordance with the set irradiation conditions to the hand piece unit 30 to drive the motors 33a and 33b, thereby swinging the mirrors 32a and 32b respectively. The swinging mirrors 32a and 32b reflect the treatment beam delivered in the hand piece unit 30 to scan the treatment beam over the treatment part so as to irradiate beam spots within the irradiation area in accordance with the scanning pattern (scanning sequence) determined based on the set shape and size of the irradiation area (and also the irradiation density). This will be mentioned later in detail.

Next, a method of scanning (irradiating) beam spots with the treatment beam is described below, referring to FIGS. 6–9 showing several selectable shapes of the irradiation area.

Prior to description of the laser scanning method using the apparatus constructed as above, the scanning method using the conventional apparatus is first explained with reference to FIG. 5.

FIG. 5 is an explanatory view of a scanning pattern (scanning sequence) for a square-shaped irradiation area with the size of 4(beam spots)×4(lines).

It is to be noted that circles in FIGS. 5–9 indicate beam spots of the treatment beam and numbers in those circles indicate a scanning sequence. The irradiation density is set to 0% where none of adjacent beam spots are overlapped each other.

It is to be noted that the treatment laser source in the present embodiment is a semiconductor laser source that emits a continuous wave (CW). This laser beam is, differing from a treatment laser beam of pulse oscillation, normally continuously emitted regardless of whether during swinging of the mirrors 32a and 32b. Accordingly, the irradiation position of the treatment beam at stop of the mirrors 32a and 32b is considered as a beam spot. In the present embodiment, however, the laser source 104 is controlled to disable the laser irradiation during swinging of the mirrors 32a and 32b. The detail thereof will be mentioned later.

The conventional laser treatment apparatus is configured so that continuous beam spots are closely adjacently arranged as shown in FIG. 5 and continuous scanning lines are adjacently arranged. This increases thermal damages to the skin of the patient. When the treatment beam is irradiated to a first beam spot (a circled FIG. 1) and continuously an adjacent spot (a circled FIG. 2), the adjacent spot is irradiated while part of heat energy at the first beam spot is being diffused to the surroundings thereof. In addition to the diffused heat energy from the first beam spot, new heat energy may be also applied to the adjacent beam spot (the position of the circled FIG. 2). This adjacent beam spot will have a larger amount of heat than the beforehand set amount of heat, which likely cause thermal damages to the skin at that beam spot.

Figure 6A:
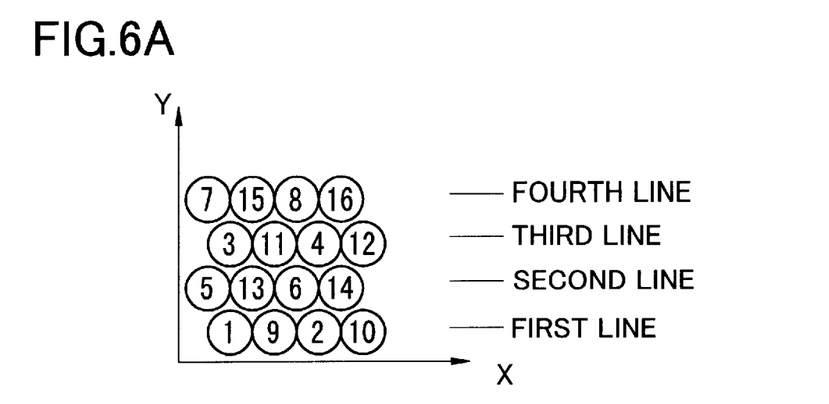
FIGS. 6A and 6B are explanatory views of a scanning pattern for a square irradiation area in a laser scanning method in the embodiment according to the present invention.
Figure 6B:
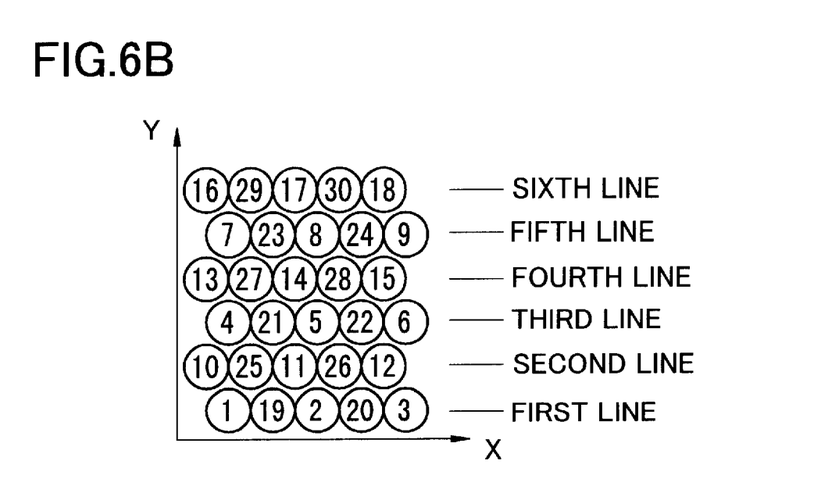

FIGS. 6A and 6B are explanatory views of scanning patterns in the laser scanning method in the present embodiment according to the present invention. Specifically, FIG. 6A shows a scanning pattern (scanning sequence) for a square irradiation area with the size of 4 (beam spots)×4 (lines), and FIG. 6B shows a scanning pattern for a square irradiation area with the size of 5 (beam spots)×6 (lines).

Irradiation is started from the leftmost beam spot (a circled FIG. 1) in the first scanning line. A second beam spot (a circled FIG. 2) to be irradiated is the next but one, not immediately adjacent one, as shown in FIG. 6A. Thus, every other spots in the first line are irradiated. When irradiation to all of alternate spots in the first line is completed, irradiation is made on the next line but one (i.e., the third scanning line), not the immediately adjacent scanning line (i.e., the second scanning line). Likewise, the treatment beam is regularly irradiated to the third scanning line, beginning with the leftmost beam spot (a circled FIG. 3), so that immediately adjacent beam spots in the identical line are not irradiated continuously.

As above, the treatment beam is earlier irradiated to odd scanning lines than even scanning lines, beginning with the leftmost spot beam in each line and irradiating alternate beam spots. Upon completion of irradiation to all of the odd lines within the set irradiation area, the treatment beam is irradiated to the second and subsequent even scanning lines, beginning with the leftmost spot beam in each line and irradiating alternate beam spots.

When irradiation to all of the alternate beam spots in the even lines are completed, returning to the first and subsequent odd lines, the treatment beam is irradiated to the remaining beam spots in the odd lines and then in the even lines. Thus, irradiation to all of the beam spots within the set irradiation area are completed.

Besides above, scanning patterns with the sizes of 6×7, 7×8, and 8×9 for the square irradiation area are stored in the memory 52. Those patterns are increased in the number of spots, but have a regular scanning sequence as with the above case.

Next, scanning patterns for other shapes of the irradiation area are described below.

Figure 7A:
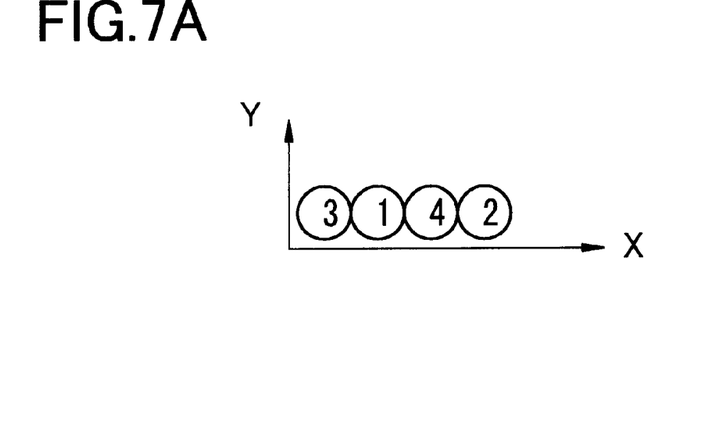
FIGS. 7A–7C are explanatory views of a scanning pattern for a linear irradiation area.
Figure 7B:
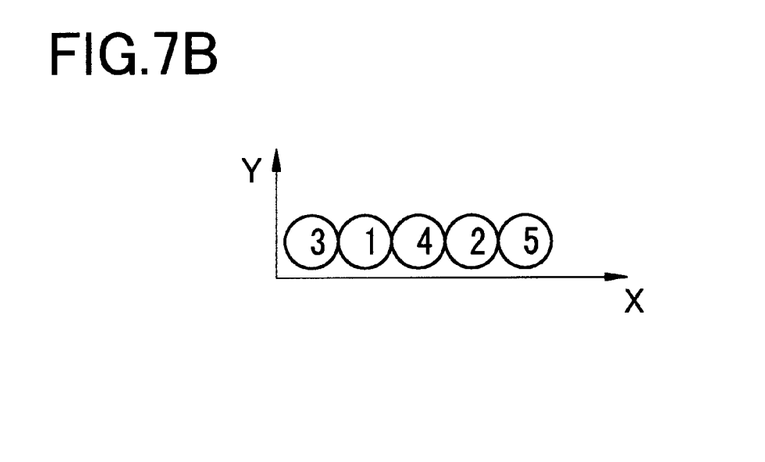
Figure 7C:
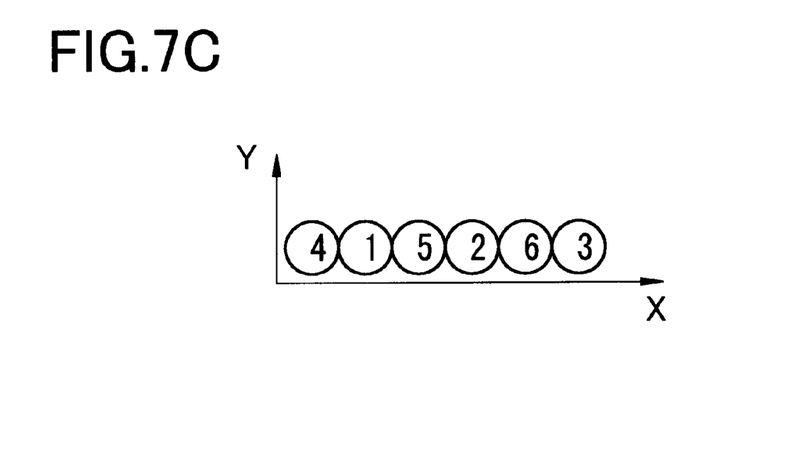

FIGS. 7A–7C show scanning patterns (scanning sequences) for a linear irradiation area, having the sizes of 4×1, 5×1, and 6×1 respectively. As in the case of the square area mentioned above, the treatment beam is irradiated to the alternate beam spots without continuously irradiating the spot adjacent to the immediately preceding irradiated spot. However, this scanning sequence begins with the leftmost spot but one, not the leftmost one. This is because, if the treatment beam is irradiated beginning with the leftmost spot in the case of the size of 4×1 (FIG. 7A), the second and third beam spots to be irradiated continuously become immediately adjacent to each other. Besides above, scanning patterns with the sizes of 7×1 and 8×1 for the linear irradiation area are stored in the memory 52. Those patterns are increased in the number of spots, but have a regular scanning sequence as with the above case.

Figure 8A:
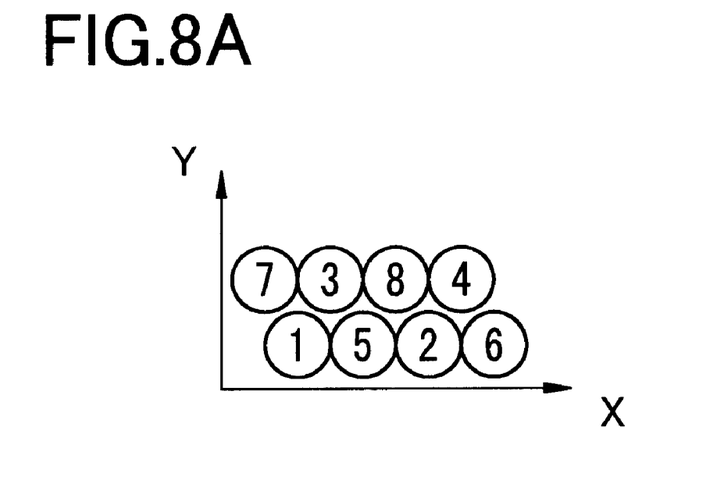
FIGS. 8A and 8B are explanatory views of a scanning pattern for a rectangular irradiation area.
Figure 8B:
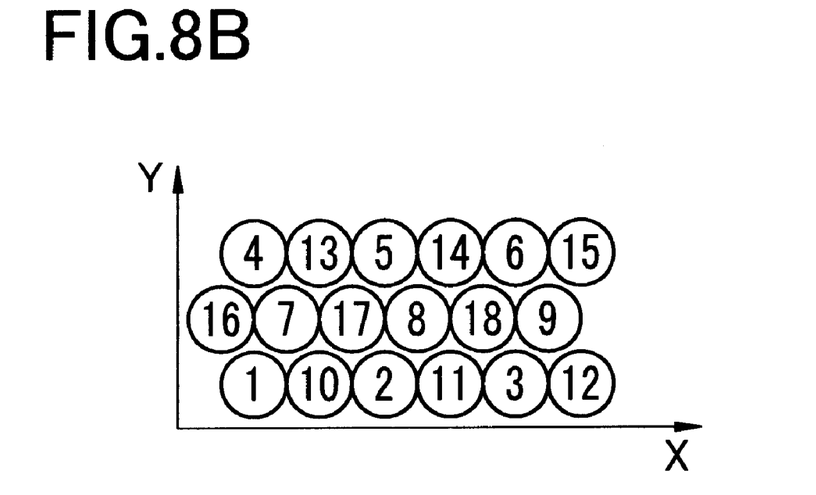

FIGS. 8A and 8B are scanning patterns (scanning sequences) for a rectangular irradiation area, having the sizes of 4×2 and 6×3 respectively. In the same manner as in the above case, the treatment beam is irradiated to alternate spots in each line and alternate lines. In the case of FIG. 8A, if the irradiation starts from the leftmost spot in each of the first and second scanning lines, the fourth beam spot in the second scanning line and the fifth beam spot in the first scanning line to be irradiated continuously become slantwise adjacent to each other. For preventing this arrangement, the scanning pattern (sequence) for the rectangular irradiation area is determined as shown in FIG. 8A.

Figure 9A:
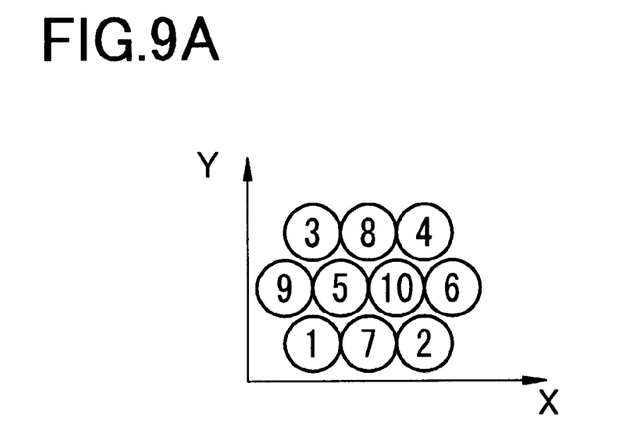
FIGS. 9A and 9B are explanatory views of a scanning pattern for a hexagonal irradiation area.
Figure 9B:
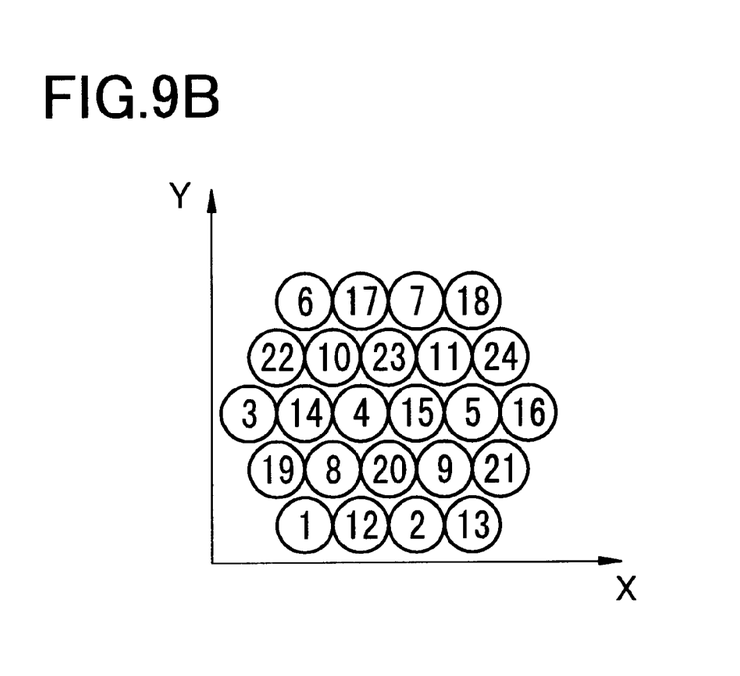

FIGS. 9A and 9B are scanning patterns (scanning sequences) for a hexagonal irradiation area, having the sizes of 4×3 and 6×5 respectively. For these patterns, the treatment beam is irradiated to alternate beam spots in each line and alternate lines as with the cases mentioned above. In the case of FIG. 9A, if the irradiation begins with the leftmost spot in each of three scanning lines, the sixth beam spot in the second scanning line and the seventh beam spot in the first scanning line become slantwise adjacent to each other. For preventing such the arrangement, the scanning pattern (sequence) for the hexagonal irradiation area is determined as shown in FIG. 9A. Besides above, scanning patterns with the size of 7×7 for the hexagonal irradiation area is stored in the memory 52. This pattern is increased in the number of spots, but has a regular scanning sequence as with the above case.

The regular scanning patterns (sequences) of beam spots to be irradiated with a treatment beam are determined in advance in correspondence with a plurality of shapes and sizes of an irradiation area and stored in the memory 52 in association with the corresponding shapes and sizes. The scanner controller 51 calls the scanning pattern corresponding to the set shape and size of the irradiation area from the memory 52 through the control unit 50 and controls to drive the motors 33a and 33b based on the scanning pattern data from the memory 52. The scanning patterns may be determined in advance in a one-by-one correspondence with a plurality of shapes and sizes of an irradiation area and irradiation density patterns and stored in the memory 52. Such the scanning patterns are determined based on a spot diameter of the treatment beam.

The above rule (or algorithm) that the treatment beam is irradiated to alternate beam spots and the rule that the treatment beam is irradiated to alternate scanning lines enable a corresponding scanning pattern to be easily obtained and determined at the time when an irradiation area pattern (shape and size, and irradiation density, etc.) is set and stored in advance in the apparatus. When a new irradiation area pattern is set, likewise, a corresponding scanning pattern can also be easily obtained and determined.

Such the scanning pattern (sequence) of beam spots may be determined by operational processing in the control unit 50 and the like based on the diameter of a beam spot, the shape and size of an irradiation area (and furthermore, the irradiation density), and the rule mentioned above. In this case, the data of the beam spot diameter and the rule should be stored in the memory 52. It may be configured so that the shape and size of an irradiation area (and the irradiation density) can be arbitrarily set, or can be once stored as the irradiation area pattern data mentioned above in the memory 52 and then selected by an operator.

The beam spot diameter may be variable. In this case, the scanning pattern (sequence) is also determined to conform to the variably set spot diameter in addition to the above conditions. Changing the spot diameter can be made by simply moving the lenses 31a and 31b on the optical axis or inserting/removing them into/from the optical axis.

As described above, the adjacent beam spots and the adjacent scanning lines will not be irradiated continuously, thus allowing sufficient time to cool the heat applied to each beam spot. Consequently, the heat energy required for depilation can be ensured while preventing application of surplus heat, so that thermal damages to the skin can be suppressed.

The present invention may be embodied in other specific forms without departing from the spirit or essential characteristics thereof. For instance, the above embodiment uses the semiconductor laser source, but not limited thereto. Other laser sources irrespective of the types of laser and the oscillation manners (continuous wave, pulse, and others) may be used in the present invention.

The scanning sequence is also not limited to the above mentioned and other sequences may be used if only adjacent beam spots within an irradiation area are not irradiated continuously. For example, irradiation may begin with the rightmost beam spot instead of the leftmost beam spot and with the even scanning lines instead of the odd scanning lines. Also, irradiation may be conducted on every three or four beam spots instead of alternate beam spots.

Next, explanation is made on a method of controlling the laser source 164 to disable the laser irradiation during swinging of the mirrors 32a and 32b (i.e., during shifting of the treatment beam from a beam spot to a next).

Figure 12:
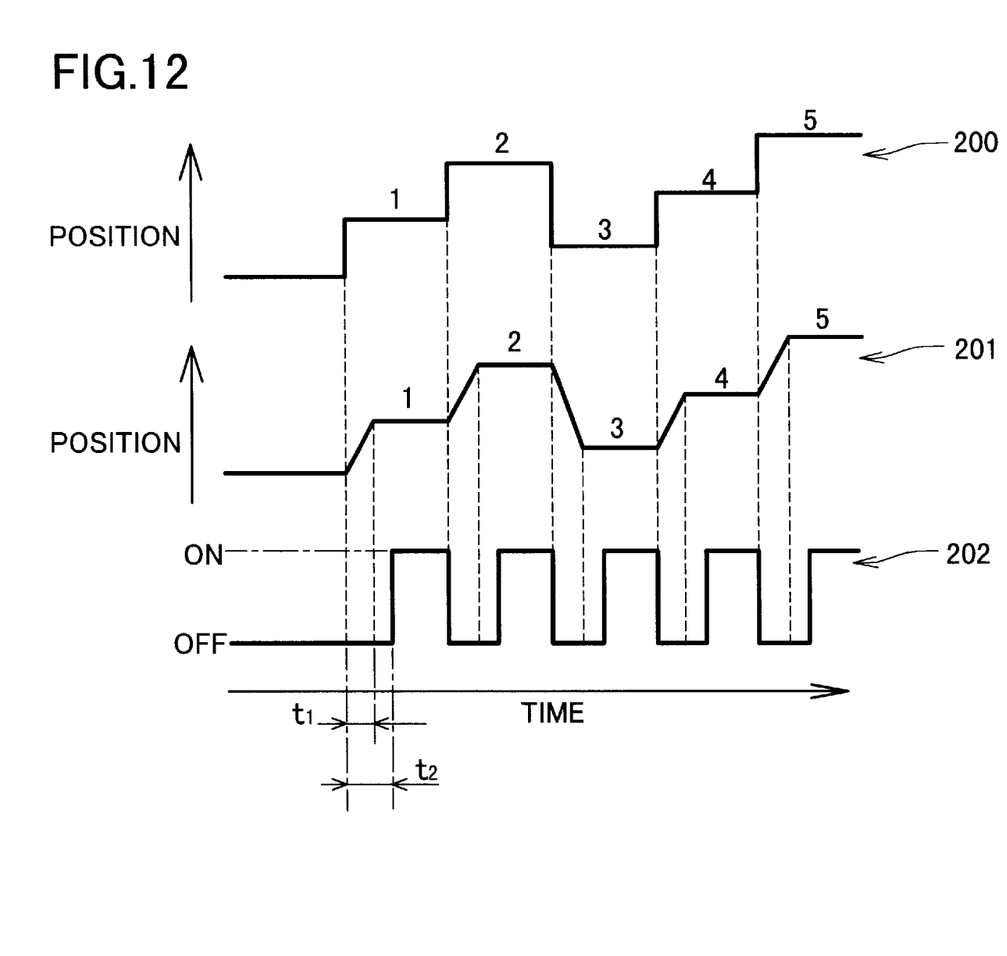
FIG. 12 is a graph for explaining a relationship between drive-control of drive motors which swing driven mirrors to allow laser scan and drive-control of a laser source.

FIG. 12 is a graph showing emission control of the treatment beam (drive-control of the laser source 104) by the control unit 50 to practice the scanning pattern shown in FIG. 7B. Reference numeral 200 is a line which schematically shows a control signal (hereinafter referred to as a POSITION INPUT signal) generated from the scanner controller 51 for controlling to drive the motor 33a (33b). The motor 33a (33b) is driven to rotate in response to the control signal, thereby changing the angle of the mirror 32a (32b), or swinging it, to shift the treatment beam to a next beam spot.

It is to be noted that numbers 1–5 assigned above the line 200 representative of the POSITION INPUT signal correspond to the beam spots shown by the circled FIGS. 1–5 respectively in FIG. 7B. Reference numeral 201 is a line which schematically shows a driving signal (hereinafter referred to as a POSITION OUTPUT signal) to be fed back from the motor 33a (33b) in relation to the POSITION INPUT signal 200.

As shown by the POSITION OUTPUT signal 201, a slight time lag $t_1$ occurs from the beginning of rotation of the motor 33a (33b) upon reception of the POSITION INPUT signal 200 to the complete stop of the rotation. The time during which the motor 33a (33b) is rotated will somewhat vary with shifting distances of the treatment beam between beam spots. In the present embodiment, accordingly, the time lag $t_1$ is experimentally determined in advance. An emission standby time $t_2$ is determined to be sufficiently longer than the time lag $t_1$. The emission standby time $t_2$ is set to 5 msec in the present embodiment.

As indicated by a line 202 showing a laser emission signal, the control unit 50 turns the emission signal 202 on after a lapse of the emission standby time $t_2$ from a change of the POSITION INPUT signal 200 generated by the scanner controller 51, thereby driving the laser source 104 to emit the treatment beam only for the set irradiation time. Subsequently, the control unit 50 disables the emission of the treatment beam for the emission standby time $t_2$. The scanner controller 51 generates a next POSITION INPUT signal 200 to drive-control the motors 33a and 33b in synchronization with the stop of operation of the laser source 104 under control of the control unit 50. It is to be noted that the generation of the POSITION INPUT signal 200 may be determined in relation to the emission standby time $t_2$ and the irradiation time. In response to the next POSITION INPUT signal 200, the motors 33a and 33b are driven to enable irradiation of the treatment beam on a next beam spot. Those operating steps are repeated until the completion of the laser irradiation to all the beam spots to be irradiated.

As mentioned above, unnecessary treatment beam is not emitted so that emission of the treatment beam is disabled during shifting of the treatment beam between beam spots, namely, during rotation of the motors 33a and 33b and thereby swinging of the mirrors 32a and 32b. This makes it possible to reduce power consumption of the laser treatment apparatus and thus extend the life of the laser source 104. Also, applying undesired heat energy to the skin can be prevented.

In the above description, the control unit 50 turns the laser emission,signal 202 into an ON state after the lapse of the emission standby time $t_2$ from a change of the POSITION INPUT signal 200 in order to disable emission of the treatment beam during operation of the motors 33a and 33b. Alternatively, the emission standby time may be appropriately determined in accordance with characteristics of the treatment beam and using conditions of the apparatus.

The emission timings of the treatment beam may be controlled based on a state of a scanning position of the treatment beam, instead of the time mentioned above. For instance, it is conceivable to compare between the POSITIONAL INPUT signal 200 and the POSITION OUTPUT signal 201 so that the emission of the treatment beam may be controlled at timings corresponding to waveform variations of both the signals.

In the above embodiment, a galvanomirror is used as the driven mirror and drive motor. Instead of it, any unit or device may be used if only it can shift the treatment beam from a beam spot to another (a next) in correspondence with start/stop of operation of the drive motor.

Although the laser emission control is performed by drive-control of the laser source in the above embodiment, it may be controlled by insertion/removal of a shutter and others with respect to an optical path of the treatment beam.

According to the present embodiment, as described above, the adjacent beam spots are not irradiated continuously with the treatment beam, keeping a sufficient heat damping time, thus preventing surplus heat energy from being supplied to the skin and suppressing resultant thermal damages.

Furthermore, the scanning sequence of beam spots can be easily determined without requiring complicated operations.

Also, according to the present embodiment, the laser irradiation can be carried out in an appropriate, efficient manner.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for performing treatment for a treatment part of a patient by irradiating the part with a treatment laser beam, the apparatus including:
   a light delivery optical system provided with a laser source for emitting a treatment laser beam, for forming the laser beam emitted from the laser source into a spot beam and for delivering the beam to the treatment part;

scanning means disposed in the light delivery optical system, for scanning the beam spots of the laser beam within an irradiation area;

setting means for variably setting at least one of a shape and size of the irradiation area and size of the beam spots;

determining means for determining a scanning sequence of the beam spots to be scanned by the scanning means based on a predetermined rule; and control means for controlling laser irradiation within the irradiation area based on the determined scanning sequence, wherein the predetermined rule is a rule that the scanning sequence is determined based on the shape and size of the irradiation area and the size of the beam spot, and when the laser irradiation is required of performing on four or more scanning lines, the scanning lines are divided into two groups of alternate scanning lines so that one group includes the $1^{st}$, $3^{rd}$ . . . scanning lines and the other group includes the $2^{nd}$, $4^{th}$ . . . scanning lines, and alternate beam spots on each scanning line of the first group are scanned, alternate beam spots on each scanning line of the second group are scanned, alternately remaining beam spots on each scanning line of the first group are scanned and alternately remaining beam spots on each scanning line of the second group are scanned.

2. The laser treatment apparatus according to claim 1 further including:

memory means for storing a plurality of shapes and sizes of the irradiation area, wherein the setting means includes selecting means for selecting a desired shape and size from among the plurality of shapes and sizes of irradiation area stored in the memory means.

3. The laser treatment apparatus according to claim 1 wherein the control means disables the laser irradiation during shifting of the laser beam from a beam spot to a next in accordance with the determined scanning sequence.

* * * * *